(12) United States Patent
Coleman et al.

(10) Patent No.: US 7,805,354 B2
(45) Date of Patent: *Sep. 28, 2010

(54) COMPENSATION DATA PREDICTION

(75) Inventors: William H. Coleman, Boston, MA (US); Gregory K. Plunkett, Boston, MA (US); Andrew L. Linn, Waltham, MA (US); Keith E. Fortier, Walpole, MA (US); Yong Zhang, Needham, MA (US)

(73) Assignee: Salary.com, Needham, MA (US)

( * ) Notice: Subject to any disclaimer, the term of this patent is extended or adjusted under 35 U.S.C. 154(b) by 1320 days.

This patent is subject to a terminal disclaimer.

(21) Appl. No.: 10/502,837

(22) PCT Filed: Jun. 17, 2002

(86) PCT No.: PCT/US02/19402

§ 371 (c)(1),
(2), (4) Date: Jul. 28, 2004

(87) PCT Pub. No.: WO02/103488

PCT Pub. Date: Dec. 27, 2002

(65) Prior Publication Data

US 2005/0234759 A1 Oct. 20, 2005

(51) Int. Cl.
*G06F 17/50* (2006.01)
(52) U.S. Cl. ........................................ 705/37
(58) Field of Classification Search ............ 705/7, 705/10
See application file for complete search history.

(56) References Cited

U.S. PATENT DOCUMENTS

| 4,648,037 A | 3/1987 | Valentino |
| 5,600,554 A | 2/1997 | Williams |
| 5,819,231 A * | 10/1998 | Tremaine ............ 705/7 |
| 5,978,768 A | 11/1999 | McGovern et al. |
| 5,991,741 A * | 11/1999 | Speakman et al. ..... 705/30 |
| 6,401,079 B1 | 6/2002 | Kahn et al. |
| 6,735,571 B2 | 5/2004 | Coleman et al. |
| 6,741,993 B1 | 5/2004 | Zitaner et al. |
| 6,862,596 B2 | 3/2005 | Thomsen |

(Continued)

FOREIGN PATENT DOCUMENTS

EP   1096404   5/2001

(Continued)

OTHER PUBLICATIONS

U.S. Appl. No. 60/283,878, filed Dec. 12, 2002, Zhang.

(Continued)

*Primary Examiner*—Romain Jeanty
(74) *Attorney, Agent, or Firm*—Mintz, Levin, Cohn, Ferris, Glovsky & Popeo, P.C.

(57) ABSTRACT

A method of predicting compensation data includes obtaining compensation data, associated with a job category, with at least one datum being associated with each of a plurality of characteristics associated with the job category, determining values of factors, associated with respective ones of the characteristics, and a base value that when used as operands of a function yield estimates of the obtained data such that relationships between the estimates and corresponding obtained compensation data satisfy at least one criterion, and using a portion of the values of factors and the base value by a computer to automatically obtain estimates of compensation data.

28 Claims, 5 Drawing Sheets

U.S. PATENT DOCUMENTS

| | | | |
|---|---|---|---|
| 7,007,029 | B1 | 2/2006 | Chen |
| 7,376,569 | B2 | 5/2008 | Plunkett et al. |
| 2002/0002479 | A1 | 1/2002 | Almog et al. |
| 2002/0188542 | A1 | 12/2002 | Zhang et al. |
| 2005/0234759 | A1 | 10/2005 | Coleman et al. |
| 2006/0271421 | A1 | 11/2006 | Steneker et al. |
| 2008/0027747 | A1 | 1/2008 | McGovern et al. |

FOREIGN PATENT DOCUMENTS

| | | |
|---|---|---|
| WO | WO-9214212 | 8/1992 |
| WO | WO-02088873 | 11/2002 |
| WO | WO-02103488 | 12/2002 |

OTHER PUBLICATIONS

U.S. Appl. No. 60/298,440, filed Jan. 2, 2003, Coleman.

Coleman, *Compensation Surveys*, BostonWorks.com, May 2001, pp. 1-8.

Dolsen, *Journal of Cash Management 1991 Compensation Survey*, Jan. 1992, Journal of Cash Management, vol. 12, n1, p. 58-66, Dialog file 15 Accession No. 00598335.

Kaplan Essays on Incentives and Compensation, *Theory and Evidence (CEO, Performance Pay, Productivity*, 1998, Corporate Source/Institution: Cornell University.

Monster.com—Websites Mar. 26, 2001.

SalaryExpert.com—Websites, Mar. 26, 2001 and Jul. 26, 2004.

www.careerbuilder.com; anylinkage wayback machine Feb. 29, 2000. Retrieved on Jun. 20, 2005.

www.erieri.com; anylinkage wayback machine, Mar. 2, 2000. Retrieved on Jul. 15 and 24, 2004.

* cited by examiner

COMPENSATION DATA PREDICTION

FIELD OF THE INVENTION

The invention relates to providing compensation data and more particularly to processing compensation data to determine and provide predicted compensation data.

BACKGROUND OF THE INVENTION

Employers, as well as persons seeking jobs, typically want to know how much compensation is appropriate and/or how much others in similar situations are paid. The compensation may take many forms such as base pay, bonus pay, stock, stock options, incentives, benefits (e.g., medical, dental, optical, etc.), and perquisites. How much and in what form a person will be compensated is typically a driving influence in whether the person is interested in obtaining and continuing in a particular job. Thus, compensation information is often desired by individual persons seeking jobs and entities offering jobs.

Data regarding compensation from which a person can accurately assess the compensation provided for a particular job is often not available. For example, while compensation data reporting companies exist, employers may not provide compensation data to these companies at all, or not for a particular job of interest to an employer or a job seeker. Further, data may not be available for positions in a particular region that the seeker is interested in, or for the size of organization, the particular job, or the industry sought by the job seeker. Also, while compensation data may be available, there may be so few matching or relevant data points that the user is unable to determine what compensation should be expected.

SUMMARY OF THE INVENTION

In general, in an aspect, the invention provides a method of predicting compensation data, the method including obtaining compensation data, associated with a job category, with at least one datum being associated with each of a plurality of characteristics associated with the job category, determining values of factors, associated with respective ones of the characteristics, and a base value that when used as operands of a function yield estimates of the obtained data such that relationships between the estimates and corresponding obtained compensation data satisfy at least one criterion, and using a portion of the values of factors and the base value by a computer to automatically obtain estimates of compensation data.

Implementations of the invention may include one or more of the following features. Using the portion of the values of factors and the base value includes using each combination of values of factors for which values are determined. The method further includes deriving reference data using the obtained compensation data and the values of factors, and aggregating the reference data to determine the base value. The aggregating comprises averaging the reference data. The method further includes comparing estimated compensation data with obtained compensation data of the same job and having the same associated characteristics as the estimated compensation data, adjusting the values of the factors as appropriate depending upon results of comparing the estimated and obtained compensation data, and repeating the deriving, aggregating, using, comparing, and adjusting until comparing the estimated and obtained compensation data satisfy the at least one criterion.

Implementations of the invention may also include one or more of the following features. The characteristics are scope criteria associated with jobs. The characteristics include at least one of geographic region, size of organization, industry, and seniority. The method further includes comparing indicia associated with obtained data and estimated data respectively. The indicia are of estimated and obtained data. The relationships are differences between estimated and obtained data associated with the same job and same characteristics. The at least one criterion is that the differences are within a magnitude limit. The relationships are ratios between estimated and obtained data associated with the same job and same characteristics. The at least one criterion is that the ratios are within a magnitude limit.

Implementations of the invention may also include one or more of the following features. The obtained data are associated with at least two job categories, and the method further includes determining a job-to-job factor relating compensation data of a first job category to compensation of a second job category, and applying the job-to-job factor to a selected datum of the first job category to determine a datum of the second job category. The selected and determined data are compensation data. The selected and determined data are values of factors. The method further includes combining the estimates of compensation data and the obtained compensation data. The combining includes weighting at least one of the estimates of compensation data and the obtained compensation data. The method further includes transmitting indicia of the estimates of compensation data via a communications network to a destination for display at the destination.

In general, in another aspect, the invention provides a system for estimating compensation data, the system including a communications network interface configured to be coupled to a communications network, a storage device configured to store compensation data, and a processor coupled to the network interface and to the storage device and configured to: calculate a base value associated with the stored compensation data by solving a relationship for reference data using the stored compensation data and predetermined values of training factors associated with scope criteria of the compensation data, the relationship relating the reference data, compensation data, and the values of the training factors, the processor further configured to calculate the base value by combining the reference data to determine the base value; and determine estimated compensation data by solving the relationship for the compensation data using values of the training factors and the base value.

Implementations of the invention may include one or more of the following features. The processor is further configured to compare the estimated compensation data and the stored compensation data and to provide indicia of the comparison. The processor is further configured to re-calculate the base value and re-determine estimated compensation data using different values of factors if relationships between the estimated compensation data and the stored compensation data fail to satisfy at least one predetermined criterion. The relationships are differences and the at least one predetermined criterion is whether the differences are within a threshold value. The relationships are ratios and the at least one predetermined criterion is whether the ratios are within a threshold value.

Implementations of the invention may also include one or more of the following features. The processor is further configured to determine initial values of the factors by combining compensation data points associated with a particular job to determine a neutral data point and comparing the neutral data point with a data points associated with the scope criteria. The system further includes a user interface coupled to the processor and configured to provide values of the factors. The processor is further configured to combine the estimated and stored compensation data. The processor is further configured to provide the combined compensation data to the network interface. The processor is configured to receive indicia of weighting of the stored and estimated compensation data and to provide weighted combinations of the stored and estimated compensation data to the network interface for display on a display device coupled to the communications network.

In general, in another aspect, the invention provides a method of predicting compensation data, the method including collecting compensation data for each of a plurality of jobs, at least one datum being associated with each of a respective plurality of associated scope criteria for each job, deriving reference data for each of the plurality of jobs in accordance with a function relating collected compensation data, the reference data, and respective training factors indicative of the respective associated scope criteria, aggregating the reference data associated with each of a plurality of jobs to determine respective aggregated reference data, using a portion of the respective training factors and the respective aggregated reference data to determine respective estimated compensation data for each of the plurality jobs, comparing the respective estimated compensation data with collected compensation data of the same job and having the same associated training factors, iterating the respective training factors as appropriate, and repeating the deriving, aggregating, using, comparing, and iterating until the compared estimated and collected compensation data satisfy at least one comparison criterion.

Implementations of the invention may include one or more of the following features. The using determines estimated compensation data for all combinations of associated training factors for each of the jobs. The method further includes determining at least one job-to-job training factor associating compensation data of a first job to compensation data of a second job, the method further comprising estimating compensation data of the first job for a combination of training factors using estimated compensation data of the second job with the same combination of training factors.

Various aspects of the invention may provide one or more of the following advantages. Compensation data may be estimated for jobs. Estimated compensation data for a job may be derived from actual data for one or more other jobs having one or more characteristics that make the actual compensation data relevant to the job whose compensation data are estimated. Answers to compensation-data-related questions may be provided in the absence of actual data providing the answers. Compensation data may be provided to inquirers indicating on how much actual data the provided data are based. Actual and estimated compensation data may be combined to provide hybrid compensation data. Compensation data can be estimated in a methodological and consistent manner. Compensation data estimates can be done in a consistent manner and can be determined and provided to users with quick turnaround times from data collection. Anomalies in surveys and other market compensation reports can be mitigated in a consistent manner so that collected and estimated data are individually and collectively consistent and reasonable.

These and other advantages of the invention, along with the invention itself, will be more fully understood after a review of the following figures, detailed description, and claims.

DETAILED DESCRIPTION OF PREFERRED EMBODIMENTS

Exemplary embodiments of the invention provide techniques to collect, store, analyze, predict, project, and report compensation data. Compensation data can include base pay, bonuses, cash incentives, commissions, stock, stock options, benefits, perquisites, etc. Exemplary embodiments of the invention can collect compensation data from a variety of sources. The compensation data can be segmented, e.g., based upon various scope criteria. Values of factors associated with the scope criteria can be derived from the collected data and adjusted to help predict compensation data. The factor values can be used to predict other compensation data for which no data were collected, and/or for which compensation data were collected. If compensation data were collected, the collected compensation data can be combined with estimated data meeting the same or similar scope criteria. Compensation data, be it predicted, collected, or a combination of these can be presented to a user for analysis. Other embodiments are within the scope of the invention.

Figure 1:
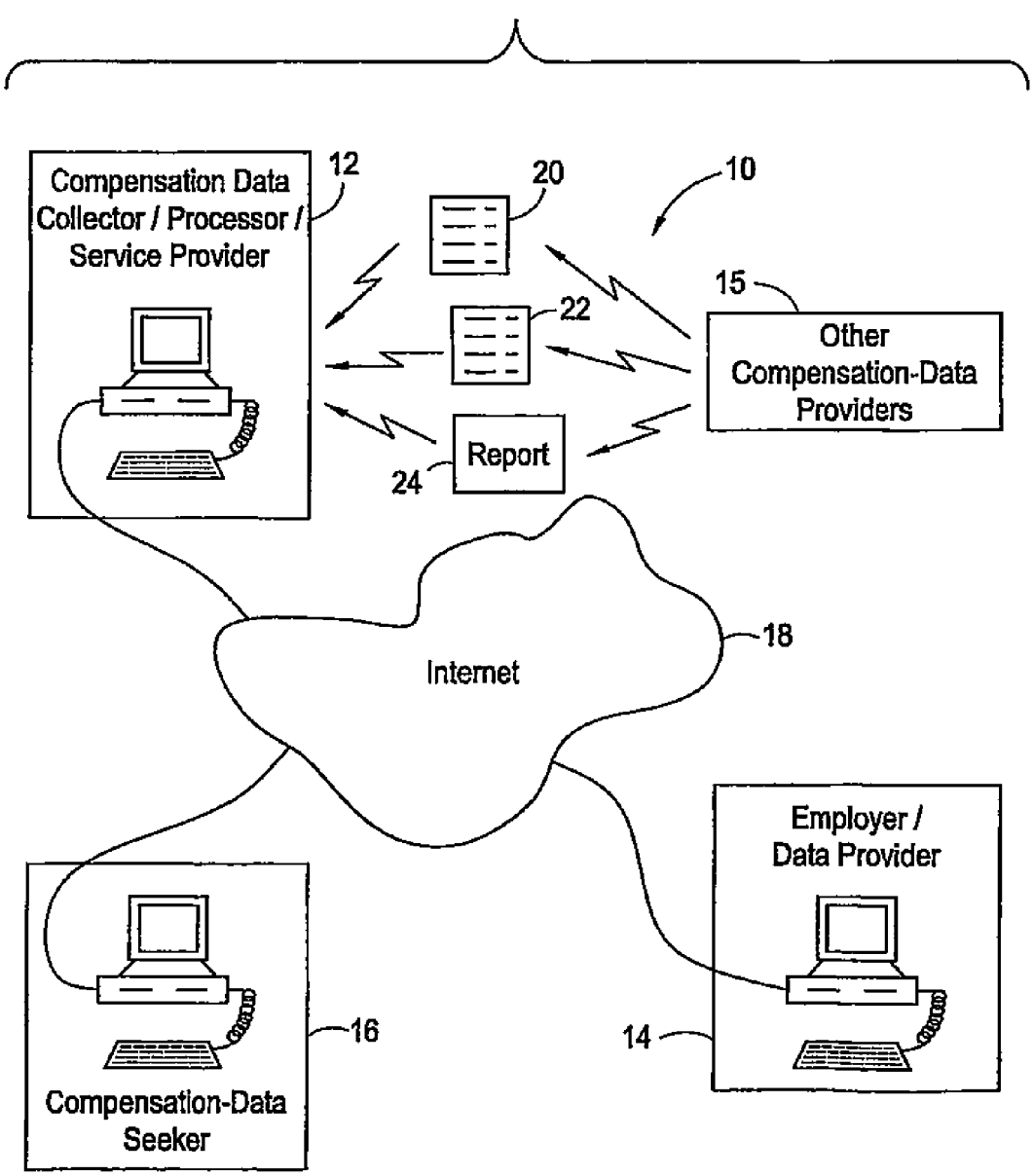
FIG. 1 is a simplified diagram of a compensation system.

Referring to FIG. 1 a system 10 includes a compensation data service provider 12, employer/compensation data providers 14, 15, a compensation-data seeker 16, and a communication network 18, here shown as the Internet as an illustrative, but not limiting, example. The service provider 12, seeker 16, and data provider 14 are configured and coupled to communicate with each other via the network 18. The other compensation-data providers are configured to provide data to the service provider 12 through other means, such as by mail.

The employer 14 and the other compensation-data providers 15 are configured to provide compensation data to the service provider 12. The employer/compensation data provider 14 can provide compensation data to the service provider 12 electronically via the network 18. For example, in response to inquiries (e.g., by the service provider 12), the employer 14 may provide data from a computer via the network 18 as shown. While only one employer 14 is shown, more employers 14 may be set up to provide compensation data regarding their employees, or other persons. Further, the other compensation-data providers 15 (that may also be employers) can respond to inquiries to provide compensation data to the service provider 12 in various forms, such as surveys 20, 22, reports 24, etc. The surveys 20, 22 may be in a form to be entered into storage at the service provider 12 manually, such as the survey 20, or may be in a machine-readable form such as a punchcard or a standard fill-in-the-bubble form 22 as shown that can be scanned.

Figure 2:
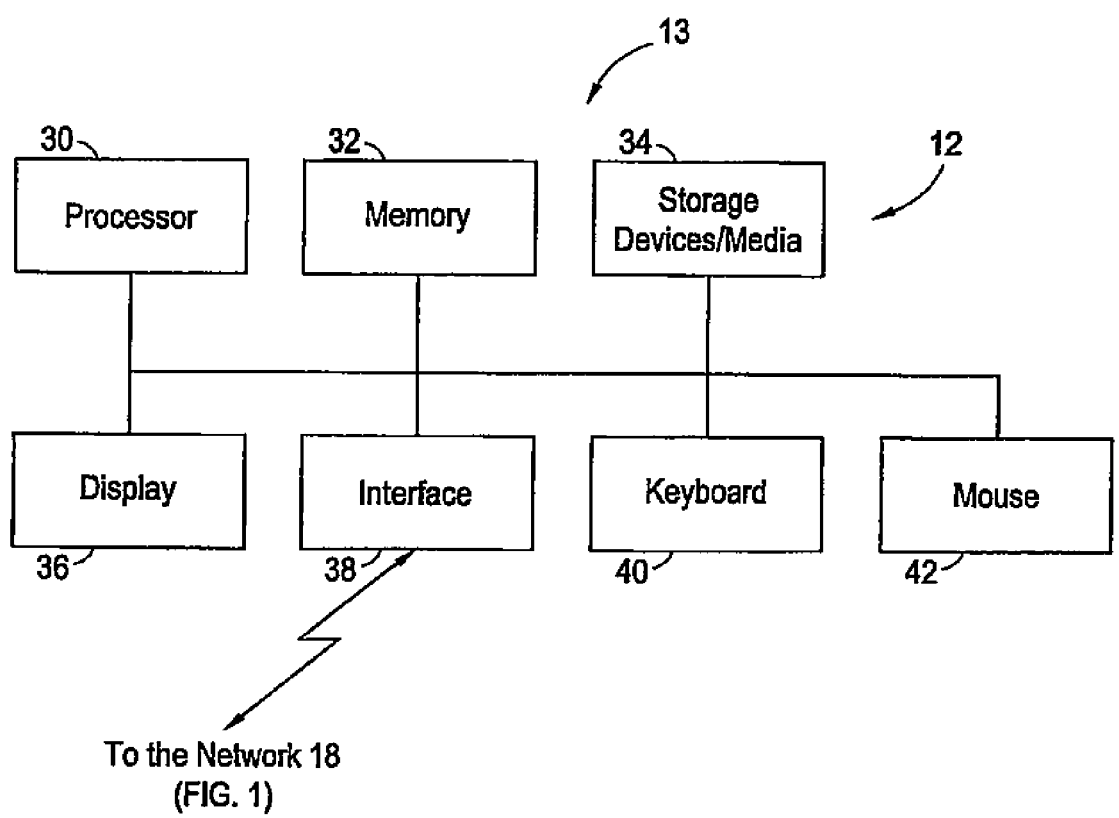
FIG. 2 is a simplified block diagram of a computer of a service provider shown in FIG. 1.

Referring also to FIG. 2, the service provider 12 comprises a computer 13 including a processor 30, memory 32, storage devices/media 34, a display 36, an interface 38, a keyboard 40, and a mouse 42 all coupled together with a bus 44. The storage devices/media 34 may include one or more databases for storing large amounts of compensation data. Databases may also be disposed separately from the computer 13 and accessible via the interface 38. The memory 32 may include Read-Only Memory (ROM), and/or Random-Access Memory (RAM). The storage devices/media 34 include hard disk drives, floppy disk drives, CD-ROM drives, DVD drives, and the like. The display 36 is configured to provide visual indicia of data entered into the computer 13, or processed by the processor 30. The keyboard 40 and the mouse 42 are configured for data entry and manipulation. Other data entry and/or data manipulation devices may be included. The interface 38 is configured to transfer data to and from the computer 13 and the network 18, and/or to and from any other desired device, that may contain a database, that is properly connected to the interface 38 (e.g., through a Local Area Network (LAN)). Other configurations of the computer 13 are possible, e.g., without the mouse 42, and/or including a touch-sensitive cursor control, etc.

The computer 13 can execute one or more software programs to process data in accordance with features described below. In particular, the storage devices/media 34 contains appropriate computer-readable and computer-executable software code instructions that can be read and executed by the processor 30 to perform below-described functions on data.

Data Collection

The service provider 12 is configured to collect and store compensation data from multiple sources. Compensation data may be individual employee compensation data or aggregated data, and may be actual data regarding actual compensation and/or approximations of actual compensation data. Compensation data may be transmitted to the service provider 12 via the network 18 from the employer/compensation data provider(s) 14, e.g., via a web-based tool. Data may also be transmitted to the service provider 12 from the data provider 14 and/or the other compensation-data providers 15 in other manners, such as via a software upload, a direct electronic feed, or other means of collecting data and/or loading data into a database. Compensation data may also be provided via hard-copy materials such as the form 20 and/or the report 24 and may be entered manually at the service provider 12, e.g., using data input apparatus 40, 42 of the computer 13. Further, data may be provided in machine-readable hard-copy form such as the form 22 and machine read at the service provider. For example, the form 22 can be scanned and information provided to the computer 13 for storage. Received data may be stored in the storage devices/media 34 of the computer 13 for further processing.

Loaded compensation data are manipulated and stored in a data library for further processing. Loaded data are tested and validated against known data points, such as market facts, manually and/or by automated procedures, e.g., for internal consistency, and to help ensure accuracy and consistency of the loaded data. The loaded data are further converted into a standardized format (e.g., mapping data categorized by a data supplier to standard categories for analysis (e.g., mapping "salary" to "base pay"). This conversion may involve altering provided numbers, e.g., by changing collected data to reduce/eliminate illogical and/or nonsensical data (e.g., if collected average base pay exceeds collected average base plus bonus). The service provider 12 can store data (e.g., the data that are, as appropriate, loaded, tested, validated, and converted) into a data library for further processing such as comparison, analysis, aggregating, and reporting as described below.

Data Training

The service provider 12 is further configured to perform data training on collected compensation data. Data training involves, among other things, iteratively adjusting training factors to use known data to derive, estimate, and/or predict unknown data. The training factors are preferably market-based factors associated with scopes of known data for various job categories. For example, known pay figures for various jobs may have associated scopes of industry, seniority, geography, organization size, etc. Thus, for each job category there may be a set of training factors for the industry the job is in, what country/state/county/town/municipality or other geographic region collected data are associated with, how big the organization is that supplied a datum (e.g., small, medium, large, or other categories of size), what seniority of the job (e.g., junior, mid-level, or senior, or Accountant I vs. Accountant II), etc. Thus, the factors may have limited values indicative of classifications or ranges of the associated scope criterion that may be associated with definitions (e.g., what constitutes a small vs. a large organization, a junior vs. a mid-level person, an Accountant I vs. an Accountant II, etc.). The values may relate to other classifications, such as what geographic region the data represents (this may be unlimited based on the level of detail desired). Any criteria may have a factor with a limited or an unlimited number of values. The training factors represent impacts of various scopes on compensation. The training factors may be dependent upon one or more other training factors. Thus, for example, the training factor for geographic region may be different depending upon whether the job is in, e.g., a large vs. a small organization. Training factors may, however, be the same for different jobs; for example, the geographic region factor may be the same for engineers and for teachers. Also, relationships between compensation indicia for different jobs may be determined to provide job-to-job extrapolation training factors.

The service provider 12 is configured to determine the training factors for data training. The factors can be determined using known collected data and a training function that relates reference data and the training factors to the collected data. The training function may take many forms, such as a linear, polynomial, or multiplicative mathematical function, etc. Preferably, the training function generally takes the form:

$$\text{collected data} = TF_1 * f(RD)\ [rel]\ TF_2 * g(RD)\ [rel]\ TF_3 * h(RD) \quad (1)$$

where $TF_n$ are the training factors, RD indicates the reference data, f, g, and h represent functions, and [rel] indicates a relationship between the terms, e.g., addition or multiplication. For example, the functions f, g, and h, etc. may be $f(x)=g(x)=h(x) \ldots =x$ and [rel] may be addition for a linear relationship such that equation (1) becomes collected data=$TF_1*RD+TF_2*RD+TF_3*RD\ldots$. Alternatively, $f(x)=1$, $g(x)=x$, $h(x)=x^2$, etc. and [rel] is addition for a polynomial relationship such that equation (1) becomes collected data=$TF_1+TF_2*RD+TF_3*RD^2\ldots$. Further, $f(x)=x$, $g(x)=1$, $h(x)=1$, etc. and [rel]=multiplication may be used such that equation (1) is a multiplicative function, becoming:

$$\text{collected data} = RD * \prod TF_n \quad (2)$$

where n=1, 2, 3, . . . up to the number of training factors used.

The service provider 12 is configured to initially set the training factor values. These initial values may be arbitrary (e.g., set to 1), and/or influenced by some or all of the collected data as determined by the computer 13 and/or human input/judgment (preferably a person knowledgeable regarding compensation practices). These influences may be determined, e.g., by averaging collected data and comparing the average with individual data associated with a particular training factor, e.g., geographic area, to determine the initial training factor for that geographic area. The average may be determined from all the collected data, but is preferably taken from a portion of the collected data that is associated with a particular job (although the portion could be selected in other ways, e.g., randomly). For example, all collected pay data for the job category of "teacher" may be averaged, and a pay datum associated with a "Boston teacher" divided by the determined average to yield the initial geographic training factor for "Boston." The same can be done using the average and a datum for an electrical engineer to determine the initial training factor for electrical engineers, etc.

The service provider 12 is configured to test the initial values of the training factors, and adjust and test the training factors iteratively as appropriate to determine refined training factors. The service provider 12 can use equation (1), the initial training factors, and the actual collected data to determine the reference data corresponding to the collected data. The service provider 12 can aggregate, e.g., average, the determined reference data to determine aggregated reference data and use the aggregated reference data and the initial training factors in equation (1) to determine estimated compensation data. The estimated compensation data can be compared with the actual collected data and the initial training factors can be adjusted based on these comparisons. Adjustments can be made automatically, e.g., by the computer 13, and/or by human input. The human input is preferably by a person with knowledge and experience regarding compensation practices/standards. The service provider 12 can repeat this computation/adjustment cycle to help the estimated and actual data converge, e.g., satisfy at least one predetermined criteria such as the estimated data being within acceptable tolerance ranges of the actual collected data (e.g., a result of subtracting and/or dividing estimated and actual data is/are within specified magnitudes). Data that appear to be anomalies may be disregarded and/or diminished and/or mitigated, etc. to help the estimated and actual data converge. The training factors when the iteration is terminated are the refined training factors. Job-to-job extrapolation training factors may be determined, e.g., by comparing computed/collected compensation data (that are preferably associated with similar scopes where such data are available), or by comparing aggregated reference data for different jobs. The service provider 12 is configured to periodically re-compute the refined training factors, e.g., monthly.

Compensation data can be estimated by the service provider 12 for the combinations of scope criteria, regardless of whether compensation data with the corresponding scope criteria were collected. The aggregated reference data and the refined training factors can be used by the service provider 12 in equation (1) to determine estimates for a complete set of compensation data, i.e., for every combination of training factors for each job category. For example, using base pay aggregated reference data for a teacher, and using equation (2), the service provider can compute the base pay for a teacher in a small school in California by multiplying the aggregated reference data by the California geographic refined training factor, and by the small organization size refined training factor, for teachers. Data may be extrapolated between job categories, e.g., with a principal's base pay being calculated from a teacher's base pay aggregated reference data by applying a teacher-to-principal training factor (e.g., using equation (2), by also multiplying by this factor). Also, training factors associated with one job may be determined by applying the job-to-job factor to data (e.g., training factors) associated with another job.

Estimated data can be used by the service provider 12 to account for anomalies and/or biases that artificially affect the collected actual data. The accounting may include weighting the data as discussed below. Collected actual data, however, are preferably not changed and the service provider 12 continues to store the collected actual data as is. The provider 12 may store the estimated data and the collected data separately.

Data Interpolation

The service provider 12 is further configured to combine estimated and actual collected compensation data. Estimated data produced by the service provider 12 is internally consistent based on a self-produced set of training factors. Combining the estimated data with actual collected data may yield a "smoothed" data set that is a blend of fact and estimated data. The service provider 12 may weight the estimated data and the actual collected data and combine the weighted data to produce an aggregated data set. For example, equal weights may be applied to estimated and collected data. Weights may also be dependent on one or more factors such as source of the data, whether the data is collected or predicted, the number of companies or individuals represented by a value (e.g., is a datum an average of data from five sources or representing 20 persons, etc.), or other factors. The combination may take various forms such as an average of all data points, or by first averaging all collected data, then averaging an estimated data point and the average of the collected data. Weights could include a zero-weighting to eliminate data from the combination, e.g., to eliminate estimated data in the presence of collected data.

Data Presentation

The service provider 12 can produce and provide a compensation data report including estimated/predicted data and/or actual collected data. The service provider can arrange the compensation data into a desired report format and provide the report to the compensation-data seeker 16 via the network 18. The data seeker 16 includes a computer and a user (not shown) of the computer. The user may be, e.g., a company that wants to know what the current compensation practices are for certain jobs and certain scope criteria so that the company can remain competitive to attract and retain employees. The user may also be, e.g., an individual wanting to know what to expect for compensation for certain jobs meeting certain scope criteria (e.g., to help the individual with compensation expectations and requests). The user can choose (e.g., using a web-based tool if the network 18 is the Internet) to have compensation data provided by the service provider 12 in a variety of forms. For example, the user may choose to see a composite interpolated set of data, each individual collected value and/or estimated datum, the user's own interpolated aggregation of the collected data and/or estimates (e.g., the user can provide weights for combining collected and estimated data), or other forms of the collected and predicted data. For instances where multiple collected compensation data points exist for a particular set of scope criteria, the user may selectively weight the collected data points individually. The service provider 12 can provide a complete set of compensation data such that the user can see information for jobs with any combination of the training factors and thus any available combination of scopes of the jobs. Data presented can also include indicia of estimated and actual collected data supporting the displayed data. For example, the number of collected data points may be displayed, or indicia may be provided as to what portion of the presented data were estimated and what portion were collected.

Operation

Figure 3:
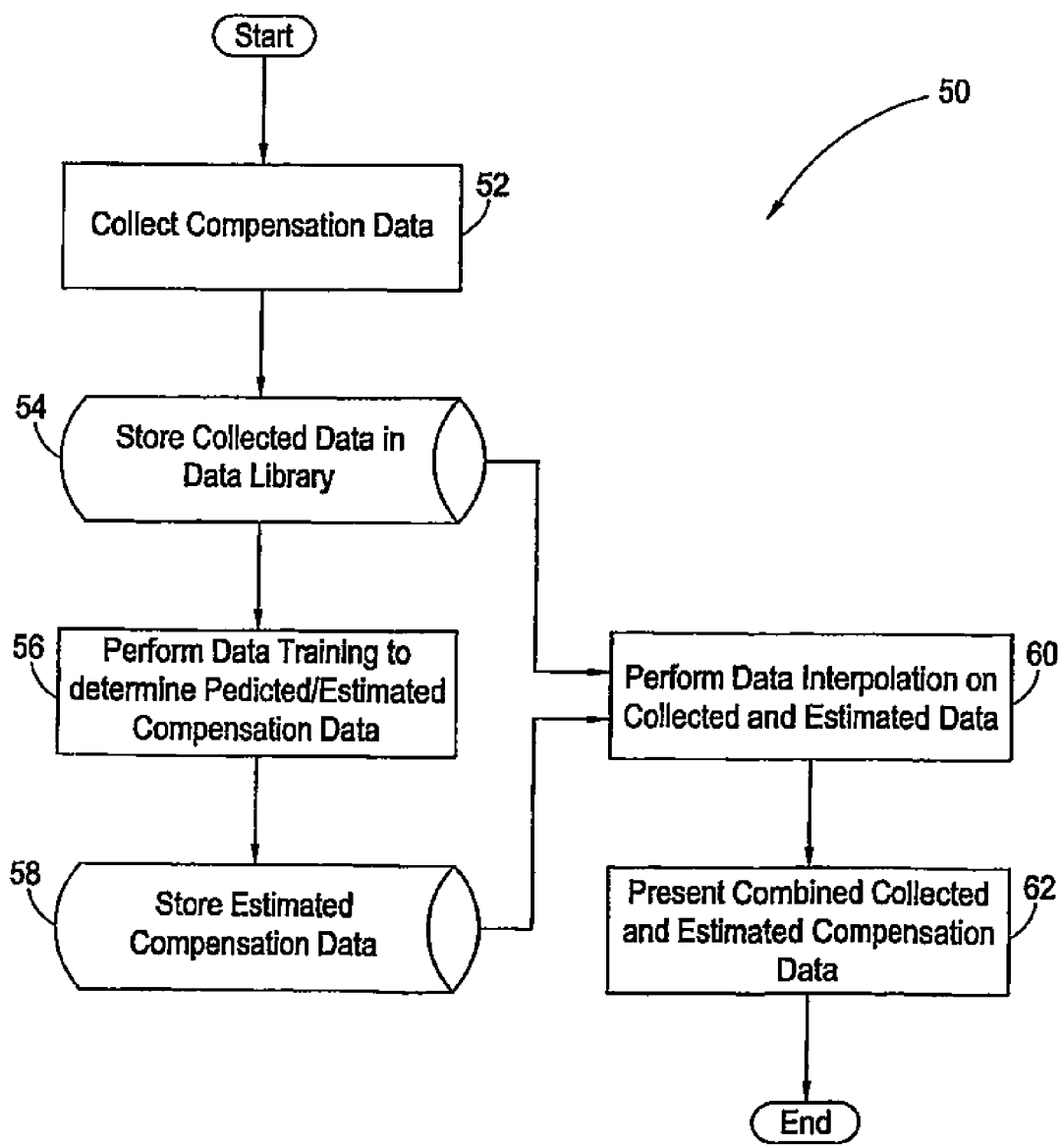
FIG. 3 is a block flow diagram of a process of collecting, training, estimating, combining, and presenting compensation data.

In operation, referring to FIG. 3, with further reference to FIGS. 1-2, a process 50 for collecting and processing compensation data using the system 10 includes the stages shown. The process 50, however, is exemplary only and not limiting.

The process 50 can be altered, e.g., by having stages added, removed, or rearranged. The process 50 is for the exemplary, not the only, situation in which the service provider 12 uses equation (2) for determining estimated compensation data, and averages reference data to determine the aggregated reference data of the determined reference data. As shown, the process 50 includes collecting compensation data, storing collected compensation data, training the stored data, estimating compensation data, interpolating the stored collected data and the trained data, and presenting the interpolated data.

Figure 4:
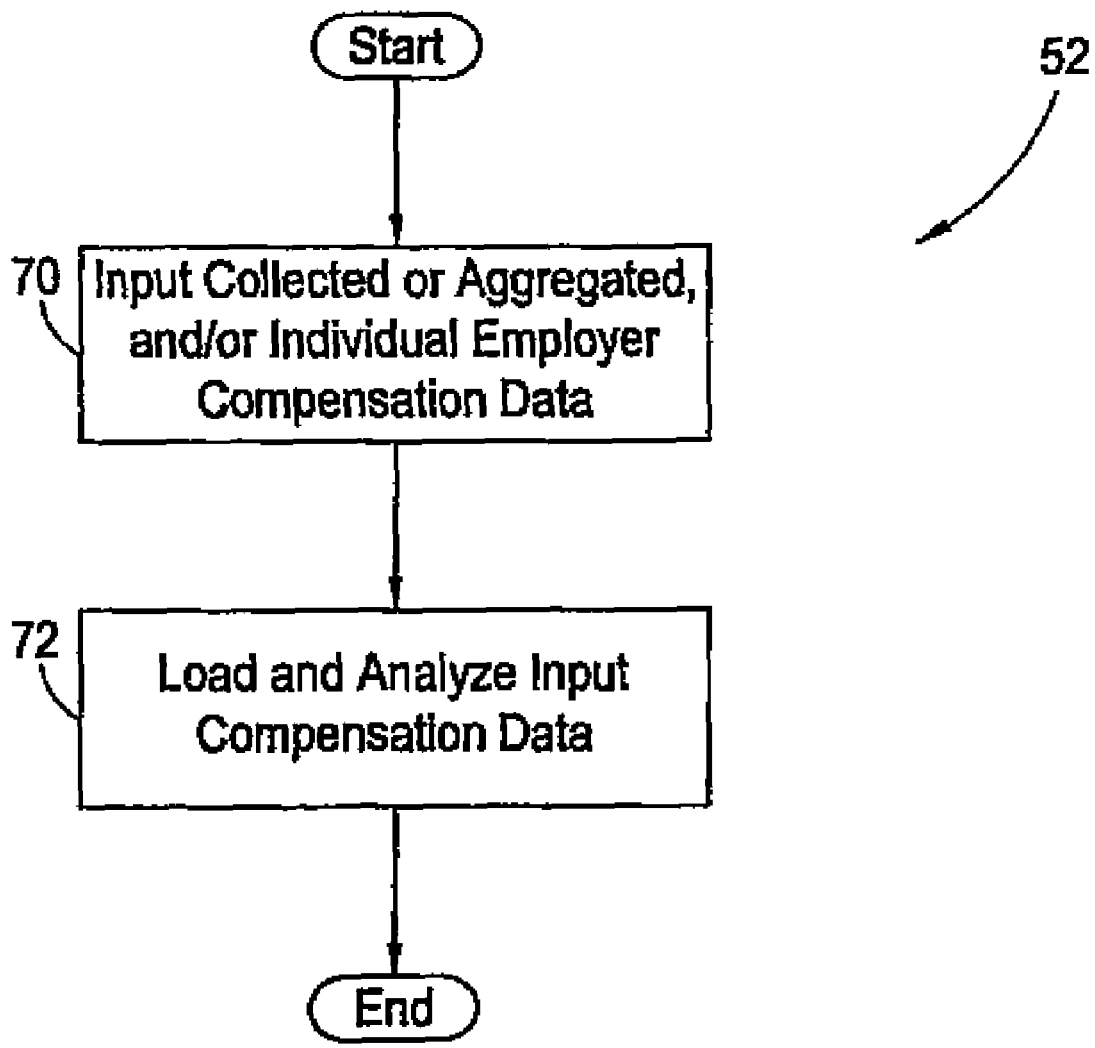
FIG. 4 is a block flow diagram of collecting compensation data.

At stage 52, the service provider 12 collects compensation data Referring to FIG. 4, the data collection stage 52 includes the sub-stages shown. The sub-stages shown, however, are exemplary only and not limiting. Sub-stages can be added, removed, or rearranged.

At sub-stage 70, published or other collections or aggregated compensation data, and individual employer compensation data, are sent to and/or acquired by the service provider 12. The data may be sent, e.g., in response to inquiries, to the service provider 12, or are acquired by the service provider 12, e.g., by soliciting responses or purchasing collections of data. The data may be sent to the provider 12 in various forms for manual and/or automatic entry, and may be for individuals, combinations of individuals, etc.

At sub-stage 72, the provider 12 loads the received/acquired data manually or automatically (e.g., with a punchcard reader, optical scanner, etc.). The loaded data are screened for internal consistency by automated procedures (e.g., a computer program) and/or with human review to analyze the data for illogical and/or nonsensical data. The service provider 12 converts the data into a standardized format, possibly adjusting data values to be stored to reduce and/or eliminate illogical and/or nonsensical data, or other data chosen to be adjusted. Stage 52 ends by proceeding to stage 54 shown in FIG. 3.

At stage 54, the service provider 12 stores the loaded, tested, converted compensation data. The data are stored in a data library database of the storage devices/media 34 of the computer 13. The data are stored in a manner to be accessible for further processing.

Figure 5:
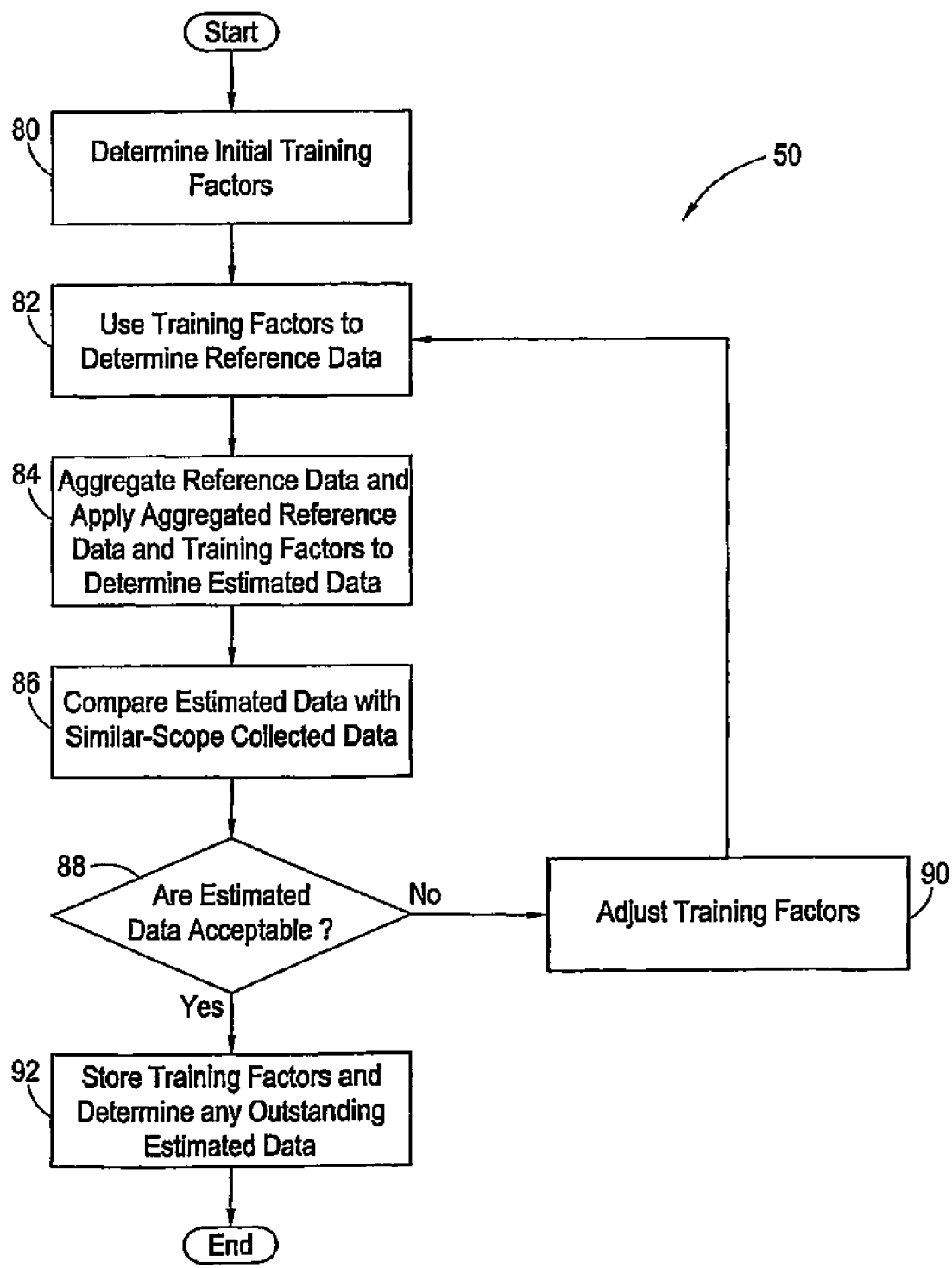
FIG. 5 is a block flow diagram of training compensation data.

At stage 56, the service provider 12 performs data training on the stored data. Referring to FIG. 5, the data training stage 56 includes the sub-stages shown. The sub-stages shown, however, are exemplary only and not limiting. Sub-stages can be added, removed, or rearranged.

At sub-stage 80, the service provider 12 determines the initial training factors. Using automated procedures and/or human input, the initial training factors are set. A person that is experienced/knowledgeable regarding compensation practices may set the values, or influence values determined, e.g., by determining a ratio of average collected data and one or more data points having a particular scope criterion. Sets of training factors are initiated for each job category desired. Training factors are initialized for each of the scope criteria to derive initial training factors for the corresponding scope criteria and the corresponding job category.

At sub-stage 82, the training factors are used to determine the reference data of equation (1). The collected data points (adjusted as appropriate) for each job category are put into equation (1) along with the training factors, and the service provider 12 solves equation (1) for the reference data for the respective job categories. In this example, the equation (2) form of equation (1) is used, and thus the reference data= (collected data)/$\Pi TF_n$.

At sub-stage 84, the reference data derived in sub-stage 82 are aggregated, and the aggregated reference data are used in equation (1) to determine estimated data. Multiple reference data are derived in sub-stage 82, preferably a datum for each collected data point. These reference data are aggregated, in this example averaged, to determine the aggregated reference data. Aggregated reference data for different job categories may be compared (e.g., a ratio taken) to determine a job-to-job extrapolation factor. The aggregated reference data and the training factors for each job are applied to equation (1), in this example taking the form of equation (2). Each combination of training factors for the respective job is used in equation (2) with the corresponding aggregated data to determine estimated compensation data for the respective job for each combination of scope criteria. Thus, even if actual data have not been collected for certain combinations of scope criteria, estimates can be obtained for these combinations using the aggregated reference data and the determined training factors, associated with that scope criteria combination, in equation (1).

At sub-stage 86, the service provider 12 compares the predicted data with the collected compensation data. Collected and predicted compensation data having similar scope criteria and the same job category are compared. For example, a difference between, or a ratio of, etc., similar data may be determined.

At sub-stage 88, the provider 12 determines whether the predicted compensation data are acceptably close to the collected compensation data. In other words, the provider 12 determines whether the current training factors adequately predict actual compensation data. If the compared data are not within acceptable limits, e.g., differences between them (or ratios of them) are greater than a threshold value, then the stage 56 proceeds to sub-stage 90, and if they are within acceptable limits, e.g., differences are less than or equal to the threshold, then stage 56 proceeds to sub-stage 92.

At sub-stage 90, adjustments are made to the training factors. The adjustments can be made automatically, e.g., according to software instructions in the computer 13, and/or manually, e.g., under influence by a person with knowledge and/or experience in compensation practices. The adjustments are made to help the predicted data better correlate to the actual collected data. The stage 56 returns to sub-stage 82 and the adjusted training factors are used in determining new reference data, etc., to re-determine predicted compensation data. This loop of sub-stages 82, 84, 86, 88, and 90 repeats until the predicted and actual data meet one or more desired criteria.

At sub-stage 92, the training factors are stored and any remaining estimated data are predicted. Preferably, at sub-stage 84, compensation data are estimated for all combinations of training factors. It is possible in sub-stage 84 above, however, to calculate estimated compensation data for fewer than all possible combinations of training factors (e.g., only those combinations for which actual collected data exist), leaving some combinations of data potentially unpredicted. In this case, at sub-stage 92, the remaining compensation data estimates are made. The stage 56 ends by proceeding to stage 58 shown in FIG. 3.

At stage 58, estimated compensation data are stored. The service provider 12 stores the compensation data estimated at stage 56 in the data library database of the computer 13 for further processing and/or display.

At stage 60, the service provider 12 performs data interpolation on the collected and estimated data. The service provider combines collected compensation data stored at stage 54 and estimated compensation data stored at stage 58 that are for the same jobs and that have the same set of scope criteria (as indicated by the training factors associated with each piece of estimated data). The data may be combined in a variety of fashions, e.g., by averaging them, by averaging all compensation data and then averaging the averaged compensation data and the estimated datum, by determining a weighted average of the data, etc. The weighting may even eliminate the actual or the estimated data (i.e., if a weighting is set to zero).

At stage 62, the combined actual and estimated compensation data are presented to the compensation-data seeker 16. The data may be transmitted to the seeker 16 electronically via the network 18. The data are sent by the service provider 12 in a format to help the data seeker user easily understand the data. The user can select to view the data in a variety of forms, e.g., by entering desired information into the computer of the data seeker 16. For example, the user may choose to view only collected data (either an average or individual values), only estimated data, or a combination of these (that may be weighted according to a user's desired weighting), etc. The user may also choose to individually weight actual data points where actual data points were collected. The service provider 12 preferably provides information as to how many actual collected data points were used in data provided to the data seeker 16, and how much of the data provided was estimated versus collected.

Other Embodiments

Other embodiments are within the scope and spirit of the appended claims. For example, due to the nature of software, functions described above can be implemented using software, hardware, firmware, hardwiring, or combinations of any of these. Features implementing functions may also be physically located at various positions, including being distributed such that portions of functions are implemented at different physical locations. Also, the job category can be treated as a training factor instead of producing sets of training factors for each job category. The job category would serve as a training factor, and other training factors could be dependent upon the job factor. Also, at sub-stages 86 and 88, instead of comparing estimated and actual compensation data and determining whether they adequately agree, the reference data and the aggregated reference data may be compared and adequacy of agreement checked. The training factors could be adjusted based on correlation between the reference data and the aggregated reference data, or still between actual and estimated compensation data.

What is claimed is:

1. A method, for use with a computer system having a processor, of predicting compensation data, the method comprising:

obtaining and storing, in the computer system having a processor, compensation data, associated with a job category, with at least one datum being associated with each of a plurality of characteristics associated with the job category;

determining values of factors, associated with respective ones of the characteristics, and a base value that, when used as operands of a function executed by the computer system having a processor, yield computer generated estimates of the obtained data such that relationships between the estimates and corresponding obtained compensation data satisfy at least one criterion;

using a portion of the values of factors and the base value, by the computer system having a processor, to automatically obtain estimates of compensation data;

deriving, using the computer system having a processor, reference data using the obtained compensation data and the values of factors;

aggregating, using the computer system having a processor, the reference data to determine the base value;

comparing, using the computer system having a processor, estimated compensation data with obtained compensation data of the same job and having the same associated characteristics as the estimated compensation data;

adjusting the values of the factors as appropriate depending upon results of comparing the estimated and obtained compensation data; and repeating the deriving, aggregating, using, comparing, and adjusting until comparing the estimated and obtained compensation data satisfy the at least one criterion.

2. The method of claim 1 wherein using the portion of the values of factors and the base value includes using each combination of values of factors for which values are determined.

3. The method of claim 1 wherein the aggregating comprises averaging the reference data using the computer system having a processor.

4. The method of claim 1 wherein the characteristics are scope criteria associated with jobs.

5. The method of claim 4 wherein the characteristics include at least one of geographic region, size of organization, industry, and seniority.

6. The method of claim 1 further comprising comparing, using the computer system having a processor, indicia associated with obtained data and estimated data respectively.

7. The method of claim 6 wherein the indicia are of estimated and obtained data.

8. The method of claim 1 wherein the relationships are differences between estimated and obtained data associated with the same job and same characteristics.

9. The method of claim 8 wherein the at least one criterion is that the differences are within a magnitude limit.

10. The method of claim 1 wherein the relationships are ratios between estimated and obtained data associated with the same job and same characteristics.

11. The method of claim 10 wherein the at least one criterion is that the ratios are within a magnitude limit.

12. The method of claim 1 wherein the obtained data are associated with at least two job categories, and the method further comprises:

determining a job-to-job factor relating compensation data of a first job category to compensation of a second job category; and applying the job-to-job factor to a selected datum of the first job category to determine a datum of the second job category.

13. The method of claim 12 wherein the selected and determined data are compensation data.

14. The method of claim 12 wherein the selected and determined data are values of factors.

15. The method of claim 1 further comprising combining, using the computer system having a processor, the estimates of compensation data and the obtained compensation data.

16. The method of claim 15 wherein the combining includes weighting at least one of the estimates of compensation data and the obtained compensation data.

17. The method of claim 1 further comprising transmitting indicia of the estimates of compensation data via a communications network to a destination for display at the destination.

18. A system for estimating compensation data, the system comprising:

a communications network interface configured to be coupled to a communications network;

a storage device configured to store compensation data; and a processor coupled to the network interface and to the storage device and configured to:

calculate a base value associated with the stored compensation data by solving a relationship for reference data using the stored compensation data and predetermined values of training factors associated with scope criteria of the compensation data, the relationship relating the reference data, compensation data, and the values of the training factors, the processor further configured to calculate the base value by combining the reference data to determine the base value; and determine estimated compensation data by solving the relationship for the compensation data using values of the training factors and the base value, and wherein the processor is further configured to re-calculate the base value and re-determine estimated compensation data using different values of factors if relationships between the estimated compensation data and the stored compensation data fail to satisfy at least one predetermined criterion.

19. The system of claim 18 wherein the processor is further configured to compare the estimated compensation data and the stored compensation data and to provide indicia of the comparison.

20. The system of claim 18 wherein the relationships are differences and the at least one predetermined criterion is whether the differences are within a threshold value.

21. The system of claim 18 wherein the relationships are ratios and the at least one predetermined criterion is whether the ratios are within a threshold value.

22. The system of claim 18 further comprising a user interface coupled to the processor and configured to provide values of the factors.

23. The system of claim 18 wherein the processor is further configured to combine the estimated and stored compensation data.

24. The system of claim 23 wherein the processor is further configured to provide the combined compensation data to the network interface.

25. The system of claim 24 wherein the processor is configured to receive indicia of weighting of the stored and estimated compensation data and to provide weighted combinations of the stored and estimated compensation data to the network interface for display on a display device coupled to the communications network.

26. A system for estimating compensation data, the system comprising:

a communications network interface configured to be coupled to a communications network;

a storage device configured to store compensation data; and a processor coupled to the network interface and to the storage device and configured to:

calculate a base value associated with the stored compensation data by solving a relationship for reference data using the stored compensation data and predetermined values of training factors associated with scope criteria of the compensation data, the relationship relating the reference data, compensation data, and the values of the training factors, the processor further configured to calculate the base value by combining the reference data to determine the base value; and determine estimated compensation data by solving the relationship for the compensation data using values of the training factors and the base value, wherein the processor is further configured to determine initial values of the factors by combining compensation data points associated with a particular job to determine a neutral data point and comparing the neutral data point with a data points associated with the scope criteria.

27. A method, for use with a computer system having a processor, of predicting compensation data, the method comprising:

collecting, and storing in the computer system having a processor, compensation data for each of a plurality of jobs, at least one datum being associated with each of a respective plurality of associated scope criteria for each job;

deriving, using the computer system having a processor, reference data for each of the plurality of jobs in accordance with a function relating collected compensation data, the reference data, and respective training factors indicative of the respective associated scope criteria;

aggregating, using the computer system having a processor, the reference data associated with each of a plurality of jobs to determine respective aggregated reference data;

using a portion of the respective training factors and the respective aggregated reference data to determine, using the computer system having a processor, respective estimated compensation data for each of the plurality jobs;

comparing, using the computer system having a processor, the respective estimated compensation data with collected compensation data of the same job and having the same associated training factors;

iterating the respective training factors as appropriate;

repeating the deriving, aggregating, using, comparing, and iterating until the compared estimated and collected compensation data satisfy at least one comparison criterion;

determining at least one job-to-job training factor associating compensation data of a first job to compensation data of a second job, and estimating, using the computer system having a processor, compensation data of the first job for a combination of training factors using estimated compensation data of the second job with the same combination of training factors.

28. The method of claim 27 wherein the using determines estimated compensation data for all combinations of associated training factors for each of the jobs.

* * * * *